United States Patent [19]

Heine et al.

[11] Patent Number: 4,876,393

[45] Date of Patent: Oct. 24, 1989

[54] β-FLUOROACYL-β-HALOVINYL ALKYL ETHERS

[75] Inventors: Hans-Georg Heine; Pieter Ooms, both of Krefeld, Fed. Rep. of Germany

[73] Assignee: Bayer Aktiengesellschaft, Leverkusen, Fed. Rep. of Germany

[21] Appl. No.: 190,781

[22] Filed: May 5, 1988

[30] Foreign Application Priority Data

May 12, 1987 [DE] Fed. Rep. of Germany ....... 3715704

[51] Int. Cl.$^4$ .............................................. C07C 49/227
[52] U.S. Cl. ...................................... 568/415; 568/392
[58] Field of Search ......................... 568/415, 416, 495

[56] References Cited

U.S. PATENT DOCUMENTS 3,259,641 7/1966 Castro ................................. 568/416
3,646,218 2/1972 Last et al. ........................... 568/415
4,590,299 5/1986 La Mattina et al. ................ 568/415

OTHER PUBLICATIONS

Angew. Chem. Int. Ed 8, 295 (1969).
Org. Prep. Proc. Int. 17, 410.
J. Org. Chem. 61, 3577 (1986).
Bull. Soc. Chim. Belg. 84, 143 (1978).
J. Org. Chem. 46, 25 7 (1981).
Synthesis 1986, 69, 340.

*Primary Examiner*—James H. Reamer

*Attorney, Agent, or Firm*—Sprung Horn Kramer & Woods

[57] ABSTRACT

Novel β-fluoroacyl-β-halogenovinyl alkyl ethers of the formula

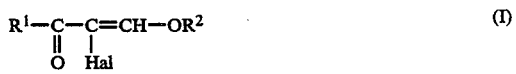 (I)

in which
 $R^1$ is a fluorinated alkyl group having 1 to 9 carbon atoms,
 Hal is a halogen atom, and
 $R^2$ is an alkyl group having 1 to 7 carbon atoms,
useful as insecticide intermediates, are produced by reacting a β-fluoroacylvinyl ether of the formula $$R^1-CO-CH=CH-OR^2 \quad (II)$$

with a halogenating agent at a temperature of $-70°$ C. to $+80°$ C., to produce a halogenation product of the formula

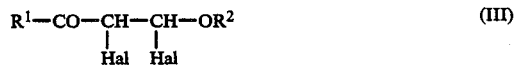 (III)

and dehydrohalogenating (III) at a temperature of $-20°$ C. to $+100°$ C.

3 Claims, No Drawings

β-FLUOROACYL-β-HALOVINYL ALKYL ETHERS

The present invention relates to new β-fluoroacyl-β-halovinyl alkyl ethers and a process for their preparation. The new β-fluoroacyl-β-halogenovinyl alkyl ethers may be used, for example, as intermediates for the preparation of biologically active compounds.

It is known to halogenate ethyl vinyl ether and to dehydrohalogenate the halogenation product with the formation of β-halogenovinyl ethyl ether [Angew. Chem. Int. Ed. 8, 295 (1969); Org. Prep. Proc. Int. 17, 410 (1985); J. Org. Chem. 51, 3577 (1986)]. The preparation of β-acyl-β-halogenovinyl ethyl ethers by this method is not known. In addition, the synthesis of 3-chloro-4-methoxy-pent-3-en-2-one by the chlorination of pentane-2,4-dione and the subsequent reaction of 3-chloropentane-2,4-dione with dimethyl sulphate/potassium carbonate in acetone is known [Bull. Soc. Chim. Belg. 87, 143 (1978)]. Similarly, 2-chloro-3-methoxy-1-phenylbut-2-en-1-one has been obtained in a mixture of its three structural isomers. Furthermore, the preparation of 3-chloro-4,4-diethoxy-butan-2-one from chloroacetone is also known [J. Org. Chem. 46, 2557 (1981)].

The β-fluoroacyl-β-halogenovinyl alkyl ethers of the formula (I) had hitherto not been prepared.

New β-fluoroacyl-β-halogenovinyl alkyl ethers of the general formula I

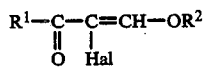

in which
  $R^1$ represents a fluorinated alkyl group having 1 to 9 carbon atoms,
  Hal represents a halogen atom and
  $R^2$ represents an alkyl group having 1 to 7 carbon atoms,
have now been found. It has furthermore been found that new β-fluoroacyl-β-halogenovinyl alkyl ethers of the general formula (I)

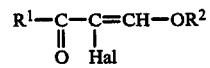

in which
  $R^1$ represents a fluorinated alkyl group having 1 to 9 carbon atoms,
  Hal represents a halogen atom and
  $R^2$ represents an alkyl group having 1 to 7 carbon atoms,
are obtained by reacting a β-fluoroacylvinyl alkyl ether of the formula II $$R^1-CO-CH=CH-OR^2 \quad (II)$$

in which
  $R^1$ and $R^2$ have the abovementioned meaning,
with a halogenating agent at temperatures of $-70°$ C. to $+80°$ C., if appropriate in the presence of a diluent, if appropriate isolating the resulting halogenation product of the general formula (III)

and dehydrohalogenating it at a temperature of $-20°$ C. to $+100°$ C.

Formula (I) provides a general definition of the new β-fluoroacyl-β-halogenovinyl alkyl ethers.

In this formula,
  $R^1$ preferably represents a fluorinated alkyl group having 1 to 3 carbon atoms,
  Hal preferably represents chlorine or bromine and
  $R^2$ preferably represents an alkyl group having 1 to 4 carbon atoms.

The following β-fluoroacyl-β-halogenovinyl alkyl ethers of the general formula (I) may be mentioned individually in addition to the compounds mentioned in the preparation examples:

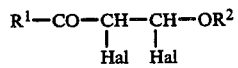

| $R^1$ | Hal | $OR^2$ |
|---|---|---|
| $CF_3$ | F | $OCH_3$ |
| $CF_3$ | F | $OC_2H_5$ |
| $CF_3$ | F | $OC_4H_9(n)$ |
| $CF_3$ | Cl | $OC_3H_7(i)$ |
| $CF_3$ | Cl | $OC_3H_7(n)$ |
| $C_2F_5$ | Cl | $OC_2H_5$ |
| $C_2F_5$ | Cl | $OCH_3$ |
| $C_2F_5$ | Cl | $OC_4H_9(n)$ |
| $C_2F_5$ | F | $OC_2H_5$ |
| $CHF_2$ | Cl | $OC_2H_5$ |
| $CHF_2$ | Br | $OC_2H_5$ |
| $CClF_2$ | Cl | $OC_2H_5$ |
| $CFCl_2$ | Cl | $OC_2H_5$ |
| $CClF_2$ | Br | $OC_2H_5$ |
| $CFCl_2$ | Br | $OC_2H_5$ |
| $C_2F_5$ | Br | $OC_2H_5$ |
| $C_2Cl_2F_3$ | Cl | $OC_2H_5$ |
| $C_3F_7$ | Cl | $OC_2H_5$ |
| $C_3F_7$ | Br | $OC_2H_5$ |

The dehydrohalogenation of the compounds, isolated if appropriate, of the formula (III) to give the compounds of the formula (I) according to the invention may be carried out, depending on the halogenating agent, either by the addition of an organic base (Hal=-halogen atom generally) or by thermal dehydrohalogenation (Hal=chlorine).

In the case of dehydrohalogenation by the addition of a base together with the use of 4-ethoxy-1,1,1-trifluorobut-3-en-2-one as component (II), elemental bromine as the halogenating agent and triethylamine as the dehydrohalogenating agent, the reaction sequence may be represented as follows:

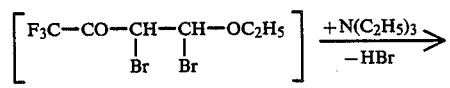

if appropriate intermediate isolation

-continued

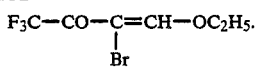

In the case of thermal dehydrohalogenation and the use of 4-ethoxy-1,1,1-trifluorobut-3-en-2-one as component (II) and sulphuryl chloride as the halogenating agent, the reaction sequence may be represented as follows:

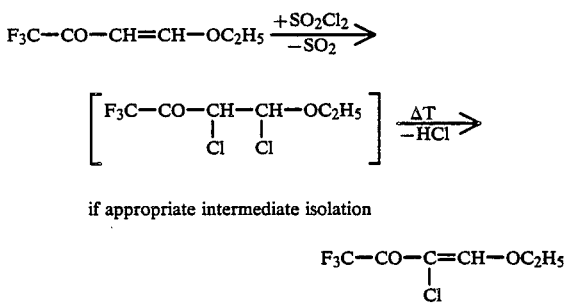

if appropriate intermediate isolation $$F_3C-CO-\underset{\underset{Cl}{|}}{C}=CH-OC_2H_5$$

The starting compounds of the general formula II required for the preparation of the new β-fluoroacyl-β-halovinyl alkyl ethers of the general formula I are known (Chem. Lett. 1976, 499) or may be synthezised in accordance with analogous reactions which have been described (Synthesis 1986, 69, 340).

Examples which may be mentioned are:
4-ethoxy-1,1,1-trifluorobut-3-en-2-one
4-n-butoxy-1,1,1-trifluorobut-3-en-2-one
5-ethoxy-1,1,1,2,2-pentafluoropent-4-en-3-one
4-methoxy-1,1,1-trifluorobut-3-en-2-one
6-ethoxy-1,1,1,2,2,3,3-heptafluorohex-5-en-4-one
13-ethoxy-1,1,1,2,2,3,3,4,4,5,5,6,6,7,7,8,8,9,9-nonadecafluorotridec-12-en-11-one
4-ethoxy-1,1-difluorobut-3-en-2-one
4-ethoxy-1-chloro-1,1-difluorobut-3-en-2-one
4-ethoxy-1,1-dichloro-1-fluorobut-3-en-2-one
5-ethoxy-2,2-dichloro-1,1,1-trifluoropent-4-en-3-one.

The conventional halogenating agents, such as, for example, chlorine, bromine, pyridinium perbromide, N-bromosuccinimide, N-chlorosuccinimide or sulphuryl chloride, may be used to halogenate the compounds of the formula (II).

The dehydrohalogenation may generally take place by means of organic bases. Such bases are, for example, alkali metal alcoholates, such as soium methylate, sodium ethylate, potassium tert.-butylate and sodium isopropylate, or tert.-amines, such as triethylamine, pyridine, dimethylaniline, methyldicyclohexylamine and, triethylenediamine (DABCO), or amidines, such as 1,5-diazabicyclo[5.4.0]-undec-5-ene (DBU) and 1,4-diazabicyclo[4.3.0]-non-4-ene (DBN). It is particularly preferred to use triethylamine.

No further elimination of hydrogen halide to give 1-fluoroacylethinyl alkyl ethers and no substitution of the halogen radical present on the vinyl radical takes place on addition of the base under the conditions of the reaction.

Surprisingly, the dehydrohalogenation may also be carried out thermally, especially when the reaction is dehydrochlorination. Thus, for example, the crude chlorination product of the general formula III ($R^1$=CF$_3$, Hal=Cl and $R^2$=C$_2$H$_5$) obtained from 4-ethoxy-1,1,1-trifluorobut-3-en-2-one and, for example, sulphuryl chloride loses hydrogen chloride unexpectedly completely when distillation is attempted at 133 mbar, forming 3-chloro-4-ethoxy-1,1,1-trifluorobut-3-en-2-one. The corresponding crude bromination product does not show an analogous behavior.

Inert, aprotic, organic solvents are suitable as the diluent for both the halogenation and also for the dehydrohalogenation by means of organic bases. These include, for example, hydrocarbons such as toluene, pentane, n-hexane, petroleum ether and dichloromethane, or ethers such as diethyl ether dioxane, methyl tert.-butyl ether and 1,2-dimethoxy ethane, or esters such as methyl acetate, ethyl acetate and dimethyl carbonate. It is preferred not to use a diluent during thermal dehydrohalogation.

The halogenation reaction temperature lies in a range from about −70° C. to +80° C., preferably about −20° C. to +20° C. Temperatures of 0° C. to +20° C. are sufficient for many halogenations. The halogenation is preferably carried out under atmospheric pressure. Analogous conditions also apply to the reaction temperature for dehydrohalogenation by means of organic bases, especially by means of tert.-amines and amidines. The reaction temperature is higher when dehydrohalogenating thermally. In general, dehydrohalogenation is carried out in the temperature range from +70° C. to +100° C. The reaction time normally lies between 0.5 and 5 hours. However, it can also be up to 24 hours, for example when tert.-amines which are slow to react are used as the bases for dehydrohalogenation.

In general, the halogenation is carried out using one mole of halogenating agent per mole of compound (II). However, it is also possible to use a small excess of halogenating agent, especially in chlorination by means of sulphuryl chloride. If an organic base is used for dehydrohalogenation, then the molar ratio of base to compound of the general formula III is at least 1:1 and is preferably 1.1:1 and at most 1.5:1.

The process according to the invention is generally carried out by initially introducing a compound of the general formula II, if appropriate in a diluent, and adding the halogenating agent dropwise with stirring, if appropriate in a diluent. In general, an exothermic release of heat occurs. The rate of addition of the halogenating agent depends on its reaction, i.e. only when the halogenating agent previously added has reacted does the addition of a further amount of halogenating agent take place. After the completion of the addition, stirring generally continues and the dehydrohalogenation of the compound of the general formula III is undertaken, if appropriate after intermediate isolation.

The dehydrohalogenation by means of organic bases is carried out by adding the organic base dropwise with stirring to the generally unisolated crude halogenation product, if appropriate in a diluent, preferably at temperatures of −20° C. to +20° C. However, the reactants may alternatively be combined in the reverse sequence, i.e. the organic base, if appropriate in a diluent, is initially introduced and the halogenation product of the general formula III in a diluent is added dropwise with stirring. In general, the dehydrohalogenation is complete after the addition of the requisite amount of organic base, so that continued stirring of the reaction mixture for a number of hours is unnecessary. Work-up takes place in a conventional manner: the reaction solution is neutralized or rendered weakly acidic by the addition of acid, for example hydrochloric acid, and the organic phase is diluted by the addition of a conventional organic solvent, washed, dried and evaporated. The new compound of the general formula I is isolated by fractional distillation under reduced pressure.

For the case of thermal elimination of hydrogen chloride, the crude chlorination product is generally heated under reduced pressure until the elimination of hydrogen chloride is completed. In general, the crude chlorination product is heated at reflux in a water jet vacuum and subsequently fractionally distilled. Refluxing is frequently unnecessary and dehydrochlorination already takes place during the distillation under reduced pressure. A homogeneous product of general formula I (Hal=Cl) is obtained by redistillation.

The β-fluoroacyl-β-halogenovinyl alkyl ethers of the general formula I, obtained by the process according to the invention, are liquids or low-melting compounds. Because of the diverse functionality (enol ether, blocked α-haloketone, blocked 1,3-dicarbonyl compound having carbonyl groups differing in reactivity and vinylogous carboxylic acid ester), the compounds of the general formula I according to the invention are important starting compounds for the preparation of biologically active compounds.

The following may be shown as an example of the further processing of the compounds according to the invention:

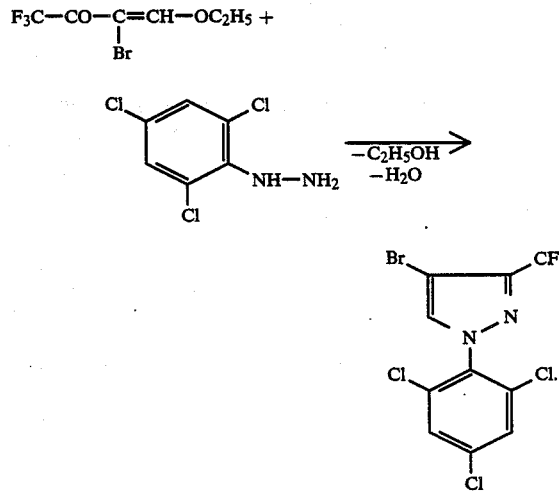

PREPARATION EXAMPLES

Example 1

21.0 g (0.165 mole) of sulphuryl chloride in 90 ml of dichloromethane are added dropwise with stirring over 30 minutes to a solution of 25.5 g (0.15 mol) of 4-ethoxy-1,1,1-trifluoro-but-3-en-2-one in 150 ml of dichloromethane. Stirring is continued for 3 hours at 0° C., the solvent and unreacted sulphuryl chloride are substantially distilled off in a water jet vacuum and 38.3 g of a pale yellow oil are obtained. The constitution is determined from the $^1$H NMR spectrum (CDCl$_3$) and is in agreement with the structure of an approximately 1:1 mixture of the diastereomers of 3,4-dichloro-4-ethoxy-1,1,1-trifluoro-butan-2-one showing signals between 1.1–1.5, 3.5–4.2, 4.75–5.0 and 5.75–5.9 ppm in the ratio 3:2:1:1. The proportion of 3-chloro-4-ethoxy-1,1,1-trifluoro-but-3-en-2-one in the mixture is less than 5%.

The diastereomer mixture is freed from residual solvent without decomposition by distillation at 1.3 mbar.

Example 2

The 3,4-dichloro-4-ethoxy-1,1,1-trifluorobutan-2-one (38.0 g) obtained according to example 1 is slowly distilled in a water jet vacuum and gives 23.9 g of a pale yellow 3-chloro-4-ethoxy-1,1,1-trifluoro-but-3-en-2-one of boiling point 84°–87° C./13.3 mbar, $n_D^{20}=1.4380$.

$^1$H NMR (CDCl$_3$): δ=1.55 t (3H, J=8 Hz), 4.40 q (2H) and 8.00 ppm s (1H). IR (CCl$_4$): $V_{CO}=1710$ cm$^{-1}$.

Example 3

28.0 g (0.22 mole) of sulphuryl chloride in 60 ml of dichloromethane are added dropwise with stirring to 39.0 g (0.2 mole) of 4-n-butoxy-1,1,1-trifluoro-but-3-en-2-one in 200 ml of dichloromethane at 0° C. After stirring for 4 hours at 0° C., the solvent and unreacted sulphuryl chloride are distilled off and the residue is distilled slowly under reduced pressure. 42.5 g of pale yellow 4-n-butoxy-3-chloro-1,1,1-trifluorobut-3-en-2-one of boiling point 105°–106° C./12 mbar, $n_D^{20}=1.4484$ are obtained.

$^1$HNMR (CDCl$_3$): δ=1.01 t (3H, J=8 Hz), 1.25–2.05 m (4H), 4.25–4.50 m (2H) and 8.00 ppm s (1H)

IR (CCl$_4$): $V_{CO}=1710$ cm$^{-1}$.

3-Chloro-4-methoxy-1,1,1-trifluorobut-3-en-2-one
4-Chloro-5-ethoxy-1,1,1,2,2-pentafluoropent-4-en-3-one and 3-Chloro-4-n-propoxy-1,1,1-trifluorobut-3-en-2-one are obtained in an analogous way.

Example 4

8.0 g (0.05 mole) of bromine in 50 ml pentane are added dropwise with stirring at −20° C. to 8.35 g (0.05 mole) of 4-ethoxy-1,1,1-trifluoro-but-3-en-2-one in 50 ml of pentane. After stirring for 1 hour at −20° C., a solution of 6.0 g (0.06 mole) of triethylamine in 150 ml of pentane is added dropwise. After stirring overnight at 20° C. the reaction mixture is poured on to ice. It is acidified by means of hydrochloric acid (pH 4–5) and extracted with petroleum ether. Washing the organic phase with saturated sodium chloride solution, drying over anhydrous sodium sulphate and evaporating the solution give 12.1 g of a yellowish liquid which is fractionally distilled under reduced pressure. 10.4 g of 3-bromo-4-ethoxy-1,1,1-trifluorobut-3-en-2-one of boiling point 100°–102° C./21.3 mbar, $n_D^{20}=1.4680$, are obtained and crystallize at −30° C.

$^1$H NMR (CDCl$_3$): δ=1.51 t (3H, J=8 Hz), 4.45 q (2H) and 8.06 ppm s (1H). IR (CCl$_4$): $V_{CO}=1710$ cm$^{-1}$.

Example 5

8.0 g (0.05 mole) of bromine, dissolved in 100 ml pentane, are added dropwise to a solution of 9.75 g (0.05 mol) of 4-n-butoxy-1,1,1-trifluorobut-3-en-2-one in 50 ml of pentane cooled to −20° C. After stirring for 1 hour at −20° C., a solution of 6.0 g (0.06 mole) of triethylamine in 100 ml pentane is added dropwise at the same temperature. After being allowed to stand overnight at 25° C., the mixture is poured into ice water and acidified by means of 1N hydrochloric acid and the phases are separated. Conventional work-up gives 12.1 g of almost homogeneous crude 3-bromo-4-n-butoxy-1,1,1-trifluorobut-3-en-2-one, which is freed from the small amount of impurities by distillation under reduced pressure. Boiling point 113°–115° C./16 mbar, $n_D^{20}=1.4640$.

$^1$H NMR (CDCl$_3$): δ=1.00 t (3H), 1.25–2.00 m (4H), 4.25–4.40 m (2H) and 8.00 ppm s (1H)

IR (CCl$_4$): V$_{CO}$=1710 cm$^{-1}$

Example 6

5.1 g (0.03 mole) of 4-ethoxy-1,1,1-trifluoro-but-3-en-2-one in 30 ml of n-hexane are reacted with 5.3 g (0.033 mole) of bromine in 18 ml of n-hexane at −20° C. After stirring for one hour at −20° C., the mixture is poured onto ice and extracted with petroleum ether. Drying of the organic phase over anhydrous sodium sulphate and evaporation under reduced pressure gives 9.6 g of crude 3,4-dibromo-4-ethoxy-1,1,1-trifluorobutan-2-one, mainly one diastereomer (according to $^1$H NMR (CDCl$_3$) analysis). Distillation under reduced pressure gives the solvent-free dibromine adduct of boiling point 43°–47° C./16 mbar (content of 3-bromo-4-ethoxy-1,1,1-trifluorobut-3-en-2-one less than 5%).

The reaction of 3,4-dibromo-4-ethoxy-1,1-trifluorobutan-2-one with triethylamine in pentane in accordance with Example 4 produced 90% of 3-bromo-4-ethoxy-1,1,1-trifluorobut-3-en-2-one.

Example 7

9.8 g (0.055 mole) of N-bromosuccinimide and 100 mg azoisobutyronitrile are added to a solution of 8.4 g (0.05 mole) of 4-ethoxy-1,1,1-trifluoro-but-3-en-2-one in 50 ml of tetrachloromethane. The mixture is then refluxed for 8 hours, the cooled solution is filtered and the filtrate is concentrated. 13.4 g of a crude product are obtained whiose distillation under reduced pressure gives 9.7 g of 3-bromo-4-ethoxy-1,1,1-trifluorobut-3-en-2-one.

In an analogous way the use of N-chlorosuccinimide gives 3-chloro-4-ethoxy-1,1,1-trifluoro-but-3-en-2-one.

Example 8: Subsequent treatment 2.3 g (0.01 mole) of 3-bromo-4-ethoxy-1,1,1-trifluorobut-3-en-2-one are added to a solution of 4.2 g (0.02 mol) of 2,4,6-trichlorophenyl-hydrazine in 100 ml of ethanol which contains 0.01 mole hydrogen bromide. The mixture is refluxed for 5 hours and then concentrated under reduced pressure, and ice water is added to the residue. Extraction with dichloromethane, washing with saturated sodium chloride solution until neutral, clarification over anhydrous sodium sulphate and concentration gives 4.6 g of a crude product, which is chromatographed on 120 g of silica gel using toluene/petroleum ether (ratio 1:1). 1.2 g of 4-bromo-1-(2,4,6-trichloro-phenyl)-3-trifluoromethylpyrazole of melting point 93°–94° C. (from petroleum ether) are obtained.

$^1$H NMR (CDCl$_3$): δ=7.50 s (2H) and 7.64 ppm s (1H).

The compound is an insecticide, as described in U.S. patent application Ser. No. 190,782, filed May 5, 1988, now abandoned.

It will be understood that the specification and examples are illustrative but not limitative of the present invention and that other embodiments within the spirit and scope of the invention will suggest themselves to those skilled in the art.

What is claimed is:

1. A β-fluoroacyl-β-halogenovinyl alkyl ether of the formula

in which
R$^1$ is a fluoroalkyl or chlorofluoroalkyl group having 1 to 9 carbon atoms,
Hal is a halogen atom, and
R$^2$ is an alkyl group having 1 to 7 carbon atoms.

2. A β-fluoroacyl-β-halogenovinyl alkyl ether according to claim 1,
in which
R$^1$ is a fluoroalkyl or chlorofluoroalkyl group having 1 to 3 carbon atoms,
Hal is chlorine or bromine, and
R$^2$ is an alkyl group having 1 to 4 carbon atoms.

3. A β-fluoroacyl-β-halogenovinyl ether according to claim 2,
in which
R$^1$ is a perfluoroalkyl group having 1 to 3 carbon atoms.

* * * * *